United States Patent [19]

Tong-Shen

[11] Patent Number: 4,491,390

[45] Date of Patent: Jan. 1, 1985

[54] AUTOMATIC LIQUID-CRYSTAL LIGHT SHUTTER

[76] Inventor: Hsieh Tong-Shen, No. 126-3, Shen Li Rd., Tso Ing, Kaohsiung, Taiwan

[21] Appl. No.: 375,570

[22] Filed: May 6, 1982

[51] Int. Cl.³ .................. G02F 1/13; H01J 40/14; H01J 1/56; G01D 5/34

[52] U.S. Cl. .................. 350/331 R; 250/208; 250/229; 250/237 R

[58] Field of Search .................. 350/331 R, 332; 250/208, 229, 237 R

[56] References Cited

U.S. PATENT DOCUMENTS

| | | | |
|---|---|---|---|
| 3,873,804 | 3/1975 | Gordon | 350/331 R X |
| 4,039,803 | 8/1977 | Harsch | 350/332 X |
| 4,071,912 | 2/1978 | Budmiger | 350/331 R X |
| 4,152,846 | 5/1979 | Witt | 350/331 R X |
| 4,155,122 | 5/1979 | Budmiger | 350/331 R X |
| 4,161,653 | 7/1979 | Bedini et al. | 350/332 X |
| 4,279,474 | 7/1981 | Belgorod | 350/332 X |

*Primary Examiner*—John K. Corbin
*Assistant Examiner*—Richard F. Gallivan
*Attorney, Agent, or Firm*—Holman & Stern

[57] ABSTRACT

An automatic liquid-crystal light shutter includes a NAND gate integrated circuit and a pair of RC oscillators operating in cooperation with two solar cells which experience internal resistance changes in response to received light. The changes in the internal resistance of the two solar cells results in a comparison signal which is applied to each of two NAND gates along with respective oppositely faced oscillator signals. When the NAND gate output signals are of different potential, the shutter passes light with little or no attenuation. If the NAND gate output signals are of the same potential, the liquid-crystal shutter becomes highly attenuated or unpassable for light. As a result, the automatic liquid-crystal shutter automatically passes low intensity light but attenuates or blocks high intensity light.

15 Claims, 7 Drawing Figures

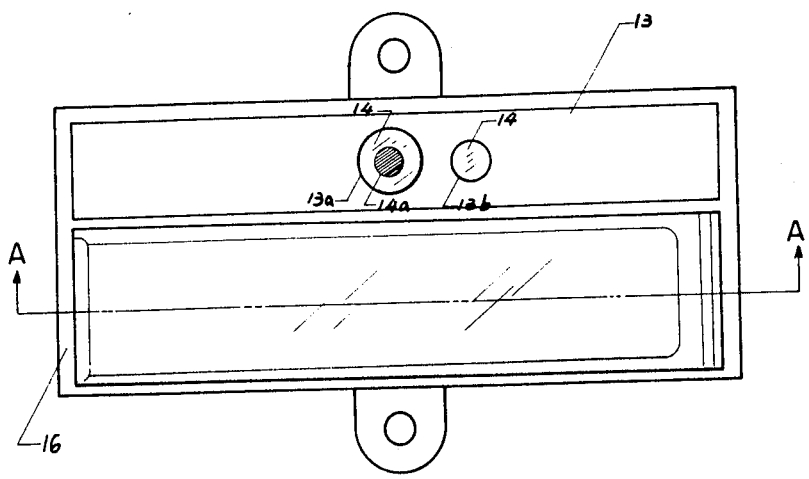
Fig: 1
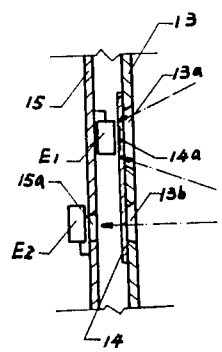
Fig: 2
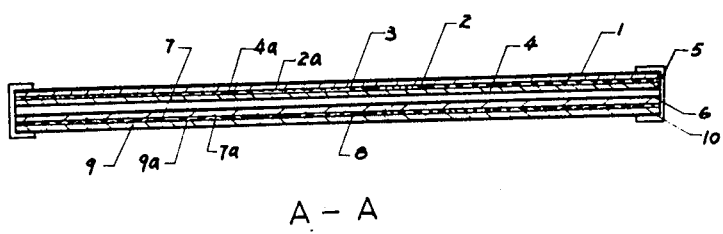
A - A
Fig: 3

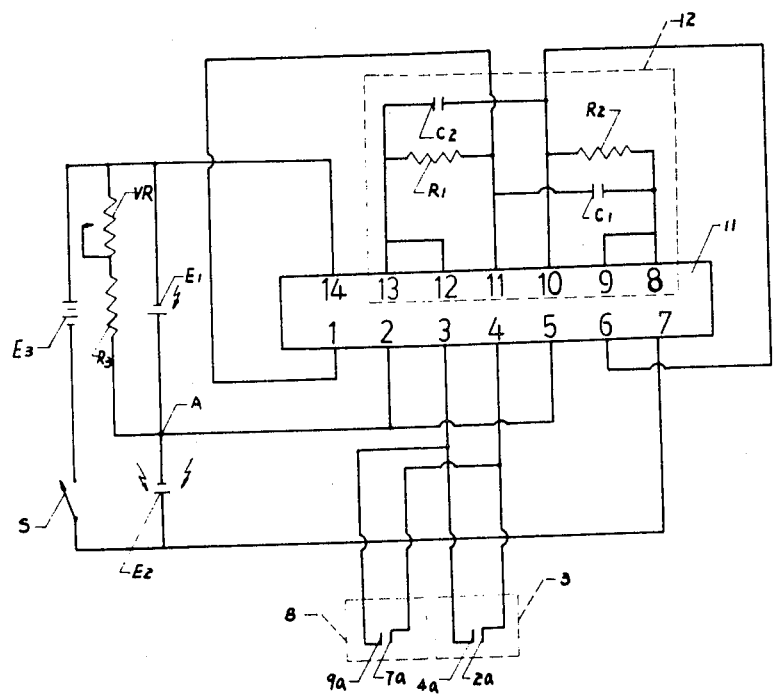
Fig: 4
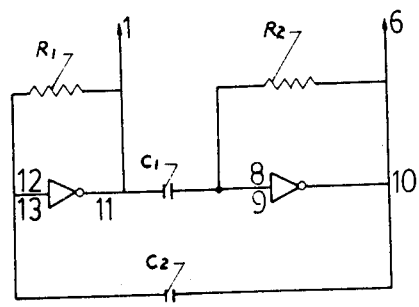
Fig: 5

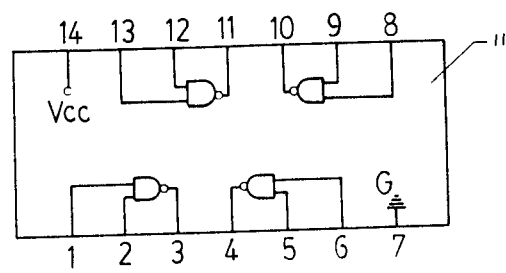
Fig: 6
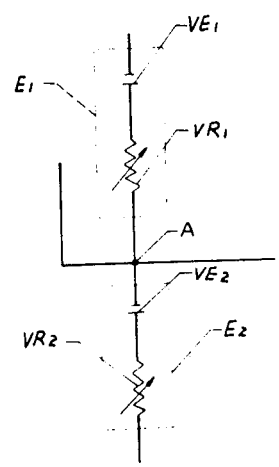
Fig: 7

AUTOMATIC LIQUID-CRYSTAL LIGHT SHUTTER

BACKGROUND OF THE INVENTION

The present invention relates to automatic liquid-crystal light shutters.

The eye is the window of a soul, says an old proverb. Our civilization can be said to be the accumulation of what human beings have seen with their eyes and what their thinking has brought about. However, it is regrettable that some of the products which have been developed by the progress of our civilization have become destructive enemies to our precious eyes. In industry, for example, our eyes take into their sight very strong light which is sparked out or otherwise emitted in the operation of electrical welding. Although welders' helmets are presently in use, such helmets have numerous inconveniences and shortcomings in such use, because a welder must hold the helmet in one hand and the welding instrument in the other hand. In addition, the welder must take a good look at the object to be welded through the helmet and then let his eyes approach the object to be welded slowly before beginning the welding work. In view of the disadvantages, the present invention has been developed and includes an automatic light shutter which makes use of liquid-crystal and electronic technology.

BRIEF DESCRIPTION OF THE DRAWINGS

In order that this invention may be clearly understood, an embodiment thereof is described by way of example with reference to the accompanying drawings wherein:

FIG. 1 is a plan view of the light shutter of the present invention;

FIG. 2 is a diagram illustrating the location of the two solar cells employed in the light shutter of the present invention;

FIG. 3 is a cross-sectional view of the light shutter taken along lines A—A of FIG. 1;

FIG. 4 is a schematic diagram of the electrical circuit of the present invention;

FIG. 5 is a schematic diagram of the equivalent circuit of the RC oscillator employed in the circuit of FIG. 4;

FIG. 6 is a schematic diagram of the equivalent logic circuit of the NAND gate integrated circuit (IC) employed in the circuit of FIG. 4; and FIG. 7 is a schematic diagram of the equivalent circuit of the solar cells employed in the circuit of FIG. 4.

DESCRIPTION OF THE PREFERRED EMBODIMENT

The present invention has primary utility in welders' helmets for attenuating or shutting off strong light but passing weak light. Nevertheless, the invention is also useful for camera shutters, space glasses, automobile rear view mirrors, and the like.

The automatic liquid-crystal light shutter of the present invention includes a light shutter structure and an operational circuit which controls the light shutter structure to render it passable or unpassable for light according to the strength or intensity of the light received. The most prominent characteristic of the circuit is the use of one solar cell which responds only to direct light, and another solar cell which responds only to side light. The two solar cells operate together in a way such that the light shutter structure becomes light-passing or light-attenuating.

All of the components of the invention are combined and set on base member 16, as illustrated in FIG. 1. The light shutter structure may be placed in the lower portion or half of base member 16. When the invention is employed in a welders' helmet, the shutter structure must be placed on the level of the workers' eyes. The make-up of the light shutter structure is described below.

Referring to FIG. 3, light-polarizing board 1, glass plate 2 with metal film coating 2a, liquid-crystal material 3, glass plate 4 with metal film coating 4a, and light-polarizing board 5 combine to constitute the first layer of the liquid-crystal light shutter structure of the present invention. Light-polarizing board 6, glass panel 7 with metal film coating 7a, liquid-crystal member 8, glass panel 9 with metal film coating 9a, and light-polarizing board 10 combine to constitute the second layer of the structure. The liquid-crystals 3 and 8 and metal films 2a and 4a are connected to the operational circuit so as to be polarized appropriately. As illustrated in FIG. 4, liquid-crystal sections 3 and 8 are connected to output terminals 3, 4 of NAND gate integrated circuit (IC) 11, thereby attaining the same potential as IC output terminals 3, 4. When there is a potential difference between these two terminals (3, 4) liquid-crystal sections 3 and 8 become passable for light; that is, light can pass through them. When there is no potential difference between the output terminals (3, 4) liquid-crystal sections 3 and 8 become unpassable for light; that is, light cannot pass through them. The principle of polarizing light in liquid-crystal material is well known and need not be explained or described herein in detail.

FIG. 4 is a schematic illustration of one operational circuit which can operate to permit the two layers of liquid-crystal material to become light-passing and light-attenuating. This operational circuit comprises a NAND gate IC 11, RC oscillators 12, two 0.5 volt solar cells E1 and E2 of variable resistance VR1 and VR2, coupling resistance R3, adjustable resistance VR, two mercury cells E3 of 3 volts, and a switch S. NAND gate IC 11 may be a model D4 011C, or the like, and includes four NAND gates. RC oscillators 12 include a first RC oscillator and a second RC oscillator which operate in opposite phase relation. These RC oscillators are contained within the dotted lines indicated by the numeral 12 in FIG. 4, the equivalent circuit of the oscillators being illustrated in FIG. 5. Resistance R1 and condenser C1 constitute the first RC oscillator; resistance R2 and condenser C2 constitute the second oscillator. Resistances R1, R2 are both 1 megohm ($10^6$ ohm) resistors while condensers C1 and C2 are both 0.005 microfarad capacitors. The oscillating period for both oscillators is $T = R1 \times C1 = R2 \times C2$, and the frequency is $$f = \frac{1}{T} = \frac{1}{R1 \times C1} = \frac{1}{R2 \times C2}.$$

The two molar cells have the same voltage and their internal resistance may vary from 1 megohm to 10 megohms. The variable resistance VR may be adjusted from 500 Kohms to 2 megohms. Coupling resistance R3 is approximately 330 Kohms. The mercury cell batteries E3 are at 3 volts and serve as the voltage source for the operating circuit. Switch S is provided to turn the circuit on and off.

FIG. 6 illustrates the equivalent logic circuit of the NAND gate IC 11. IC terminals 10, 11, 3 and 4 are the output terminals. As seen in FIG. 4, output terminal 11 is connected to input terminal 1, output terminal 10 is connected to input terminal 6, output terminals 3, 4 are connected across the liquid-crystal sections 3 and 8 at metal films 2a, 4a, 7a and 9a, and input terminals 2 and 5 are connected together to receive the same input signal.

Referring to the RC oscillator 12, the first and second oscillators provide pulses of opposite phase. The pulses provided by the first oscillator are connected to input terminal 1 of IC 11 from output terminal 11. The pulses provided by the second oscillator are connected to input terminal 6 from output terminal 10. Thus, input terminals 1 and 6 separately receive signals of opposite phase; that is, when the input signal at terminal 1 is high or logic "1", the signal at terminal 6 is low or logic "0".

The equivalent circuit for the solar cells is illustrated in FIG. 7. The solar cells may be considered to be variable voltage sources VE1 and VE2, and variable resistances VR1 and VR2 combined in series when they are in operation. The strength or intensity of the received light changes the internal resistances of the solar cells and, accordingly, input terminals 2, 5 of IC 11 may become high or low to control the light-passing and light-blocking conditions at the liquid-crystal sections.

The two solar cells E1, E2 are specially connected in the operating circuit. As illustrated in FIGS. 1 and 2, both cells E1, E2 are attached and soldered to the printed circuit board 15. Exteriorly of the printed circuit board is light-shutting board 13 with a large hole 13a and a small hole 13b defined therein. A transparent glass panel 14 is adhered to board 13 on its rearward side. The large hole 13a faces solar cell E1 and the portion of glass panel 14 registered with solar cell E1 is painted black at 14a in order that direct light cannot reach solar cell E1. Only solar cell E2 can receive direct light by virtue of a light hole 15a cut in printed circuit board 15 in registration with small hole 13b. Consequently, solar cells E1, E2 have opposite operational characteristics with respect to the direction of light impinging upon the light shutter.

The operational principle of the automatic liquid-crystal light shutter of the present invention will now be explained. It is assumed that switch S is turned on. When solar cell E1 does not receive strong side light, and solar cell E2 does not receive strong direct light, a potential difference arises between terminals 3 and 4 at IC 11. This difference in potential renders the liquid-crystal material passable to light because the voltage at point A between the solar cells E1, E2 is no less than 1.5 volts after the voltage drop through resistors VR and R3. The input signal at terminals 2, 5 of IC 11 become high and, if the input at terminal 1 is high, the output signal at terminal 3 is low. The input at terminal 6 also goes low and consequently, the output at terminal 4 is high. Thus, when the light shutter does not receive any strong light from any direction, it is in a condition for passing light.

If strong side light is directed toward the light shutter, the internal resistance of solar cell E1 drops from 10 megohms to 1 megohms and the voltage at point A becomes larger than 1.5 volts. This condition gives rise to a potential difference between terminals 3 and 4 of IC 11 in the manner described above. As a result, the light shutter is again passable to light.

In the case of high intensity direct light shining toward the shutter, the inner resistance of solar cell E2 changes. The degree of the change operates to render the voltage at point A less than 1.5 volts. The input signal at terminals 2, 5 become low and, if the input signal at terminal 1 is low, the input at terminal 6 becomes high. The output signals at both terminals 3 and 4 become high; in other words, there is no potential difference between terminals 3 and 4. This condition of no potential difference renders the liquid-crystal material non-actuated and, accordingly, in the attenuating or light-blocking state.

In summary, the present invention is an automatic liquid-crystal light shutter having a NAND gate IC, a pair of RC oscillators, mercury cells as a constant voltage source, and two solar cells, one of which only changes its internal resistance upon receiving strong side light, and the other of which only changes its internal resistance in response to direct light. The two RC oscillator circuits supply pulses of opposite phase to the terminals 1 and 6 of IC 11 through the output terminals 10 and 11. The input terminals 2 and 5 of IC 11 are connected together and receive current from the voltage source via a varying resistance VR and the solar cells. Terminals 2 and 5 attain high potential when the light shutter structure receives strong or high intensity side light or does not receive any light. This high potential combines with the pulses of opposite phase provided by the RC oscillators to establish different potentials at IC terminals 3 and 4 to provide an energizing potential to the liquid-crystal material which thereby becomes passable for light. When direct light stronger than the side light is directed toward the structure so that solar cell E2 receives the direct light and changes its internal resistance, the smaller resulting voltage drop reduces the internal resistance of solar cell E2 to provide a low potential at terminals 2 and 5. This, in combination with the pulses of different phase from the IC oscillators, results in the same potentials appearing at terminals 3 and 4. These terminals apply the equal potentials to the liquid-crystal sections which become attenuated or unpassable for light.

In case strong direct light shines towards this shutter, the inner resistance of solar cell E2 changes, and the amount changed operates to make the voltage at the point A less than 1.5 volt; then the input at leads 2,5 becomes low, and if the input at lead 1 is low, the input at lead 6 becomes high, and the output both at lead 3 and at lead 4 becomes high—in other words, there is no potential difference between lead 3 and 4; this condition of no potential difference makes the liquid-crystal stay silent and accordingly in the state of light-shutting.

What is claimed is:

1. An automatic light-responsive light shutter comprising:
light shutter means responsive to application of a control signal at a first level for passing light therethrough along a first path and responsive to application of said control signal at a second level for highly attenuating light passing therethrough along said first path;
first light responsive means for sensing intensity of direct light which strikes said light shutter means generally along said first path;
second light responsive means for sensing intensity of side light which strikes said light shutter means generally perpendicular to said first path;

circuit means for providing a comparison signal at a level which is a function of the relative intensities of direct and side light sensed at said first and second light responsive means, respectively; and control means responsive to said comparison signal for applying said control signal to said light shutter means at said first level when said comparison signal level is within a first predetermined range of levels, and for applying said control signal to said light shutter means at said second level when the comparison signal level is within a second predetermined range of levels, said first and second predetermined ranges of levels being substantially adjacent one another.

2. The light shutter according to claim 1 further comprising adjustable means for selectively varying said first and second predetermined range of levels of said comparison signal.

3. The light shutter according to claim 1 wherein each of said first and second light responsive means includes an impedance which varies with intensity of incident light, and wherein said circuit means comprises:
   a voltage source;
   means connecting said first and second light responsive means in series circuit with one another and with said voltage source; and
   means for deriving said comparison voltage from a point in said series circuit between said first and second light responsive means.

4. The light shutter according to claim 3 wherein said circuit means further comprises selectively adjustable impedance means connected in parallel with said second light responsive means for permitting selective adjustment of said first and second predetermined ranges of levels.

5. The light shutter according to claim 3 wherein said control means comprises:
   oscillator means for providing first and second alternating signals of the same frequency and opposite phase; and
   gating means responsive to said comparison signal and said first and second alternating signals for providing said control signals.

6. The light shutter according to claim 5 wherein said gating means comprises:
   first logic gate means responsive to said comparison signal and said first alternating signal for providing a first control signal component which alternates at said same frequency between two logic levels when said comparison signal level is in one of said predetermined level ranges and which remains constant at one of said two logic levels when said comparison signal level is at the other of said two logic levels; and
   second logic gate means responsive to said comparison signal and said second alternating signal for providing a second control signal component which alternates at said same frequency between said two logic levels in phase opposition to said first control signal component when said comparison signal level is in said one of said predetermined level ranges, and which remains constant at said one of said two logic levels when said comparison signal level is at the other of said two logic levels; wherein said control means includes means for applying said first and second control signal components across said light shutter means as said control signal, wherein said first level of said control signal corresponds to different logic levels existing simultaneously in said first and second control signal components, respectively, and wherein said second level of said control signal corresponds to substantially identical logic levels existing in said first and second control signal components.

7. The light shutter according to claim 6 wherein said light shutter means comprises at least one panel of liquid-crystal material, wherein said first path is substantially perpendicular to said panel, and wherein said second light responsive means is responsive to light which is directed generally parallel to said panel from an edge thereof.

8. The light shutter according to claim 6 wherein said first and second logic gating means are first and second NAND gates, respectively.

9. The light shutter means according to claim 6 wherein said first and second light responsive means are first and second solar cells, respectively.

10. The light shutter according to claim 1 wherein said control means comprises:
    oscillator means for providing first and second alternating signals of the same frequency and opposite phase; and
    gating means responsive to said comparison signal and said first and second alternating signals for providing said control signals.

11. The light shutter according to claim 10 wherein said gating means comprises:
    first logic gate means responsive to said comparison signal and said first alternating signal for providing a first control signal component which alternates at said same frequency between two logic levels when said comparison signal level is in one of said predetermined level ranges and which remains constant at one of said two logic levels when said comparison signal level is at the other of said two logic levels; and
    second logic gate means responsive to said comparison signal and said second alternating signal for providing a second control signal component which alternates at said same frequency between said two logic levels in phase opposition to said first control signal component when said comparison signal level is in said one of said predetermined level ranges, and which remains constant at said one of said two logic levels when said comparison signal level is at the other of said two logic levels; wherein said control means includes means for applying said first and second control signal components across said light shutter means as said control signal, wherein said first level of said control signal corresponds to different logic levels existing simultaneously in said first and second control signal components, respectively, and wherein said second level of said control signal corresponds to substantially identical logic levels existing in said first and second control signal components.

12. The light shutter according to claim 10 wherein said light shutter means comprises at least one panel of liquid-crystal material, wherein said first path is substantially perpendicular to said panel, and wherein said second light responsive means is responsive to light which is directed generally parallel to said panel from an edge thereof.

13. The light shutter means according to claim 10 wherein said first and second light responsive means are first and second solar cells, respectively.

14. The light shutter according to claim 1 wherein said light shutter means comprises at least one panel of liquid-crystal material, wherein said first path is substantially perpendicular to said panel, and wherein said second light responsive means is responsive to light which is directed generally parallel to said panel from an edge thereof.

15. The method of controlling visible light attenuation through a liquid-crystal panel, said method comprising the steps of:

sensing intensity of direct light impinging generally perpendicularly on said panel;

sensing intensity of side light directed towards that panel generally perpendicular to said direct light;

comparing the sensed direct light and side light intensities;

passing light through said panel with relatively little attenuation when the sensed side light intensity is approximately the same as or greater than sensed direct light intensity and when the sensed direct light intensity is below a predetermined intensity; and attenuating passage of light through said panel when the sensed direct light intensity is substantially greater than the sensed side light intensity.

* * * * *